United States Patent [19]

Eckerle

[11] 4,269,193

[45] May 26, 1981

[54] NONINVASIVE BLOOD PRESSURE MONITORING TRANSDUCER

[75] Inventor: Joseph S. Eckerle, Redwood City, Calif.

[73] Assignee: SRI International, Menlo Park, Calif.

[21] Appl. No.: 94,670

[22] Filed: Nov. 15, 1979

Related U.S. Application Data

[63] Continuation-in-part of Ser. No. 848,754, Nov. 4, 1977, abandoned.

[51] Int. Cl.³ .................................................. A61B 5/02
[52] U.S. Cl. ..................................................... 128/672
[58] Field of Search .................. 128/672, 677–683, 128/687–690

[56] References Cited

U.S. PATENT DOCUMENTS

| | | | |
|---|---|---|---|
| 3,123,068 | 3/1964 | Bigliano | 128/672 |
| 3,219,035 | 11/1965 | Pressman et al. | 128/672 |
| 3,880,145 | 4/1975 | Blick | 128/672 |
| 3,994,286 | 11/1976 | Svensson | 128/709 |

OTHER PUBLICATIONS

Pressman, G. L. et al., "A Transducer for the Continuous External Measurement of Blood Pressure", IEEE Trans. Bio–Med. Elec., Apr. 1963, pp. 73–81.

*Primary Examiner*—Robert W. Michell
*Assistant Examiner*—Francis J. Jaworski
*Attorney, Agent, or Firm*—Urban H. Faubion

[57] ABSTRACT

Intra-arterial blood pressure is noninvasively measured and monitored by an electromechanical force sensor which is made up of an array of individual pressure or force sensing elements, each of which has at least one dimension smaller than the lumen of the underlying artery wherein blood pressure is to be measured, and the individual pressure sensitive element used to monitor blood pressure is within one artery's diameter of the pressure sensitive element that generates the waveform of maximum pulse amplitude and generates a waveform having a spatially local minimum of at least one of the diastolic and systolic pressures.

9 Claims, 8 Drawing Figures

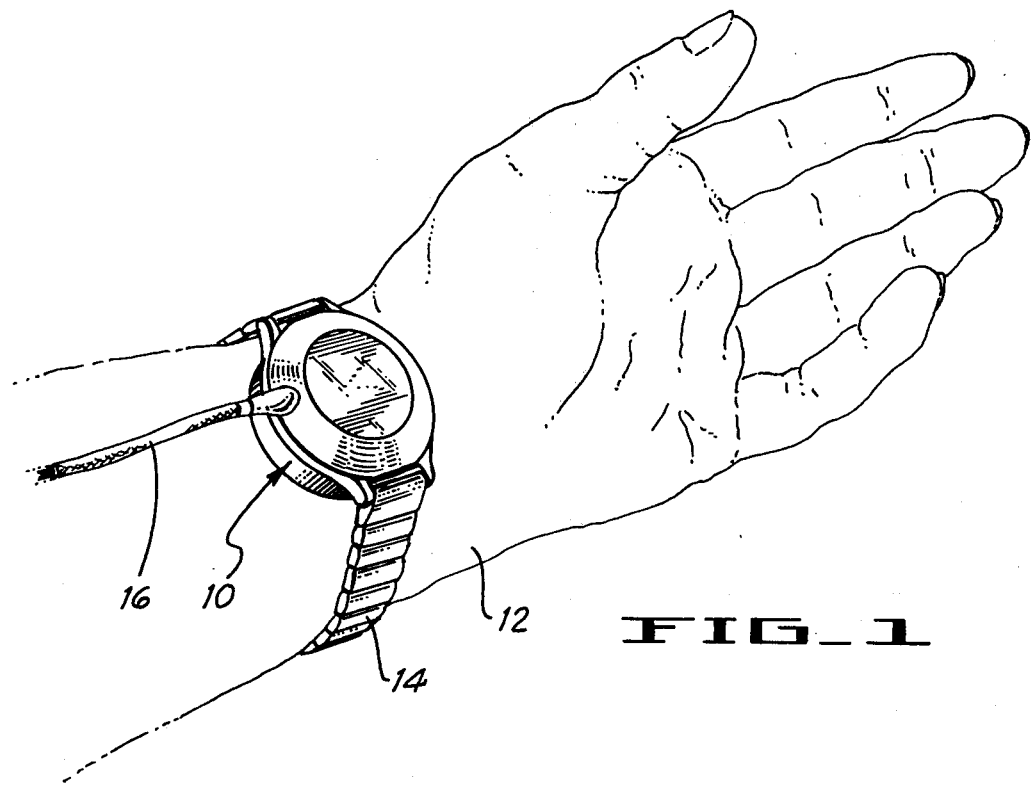
FIG_1
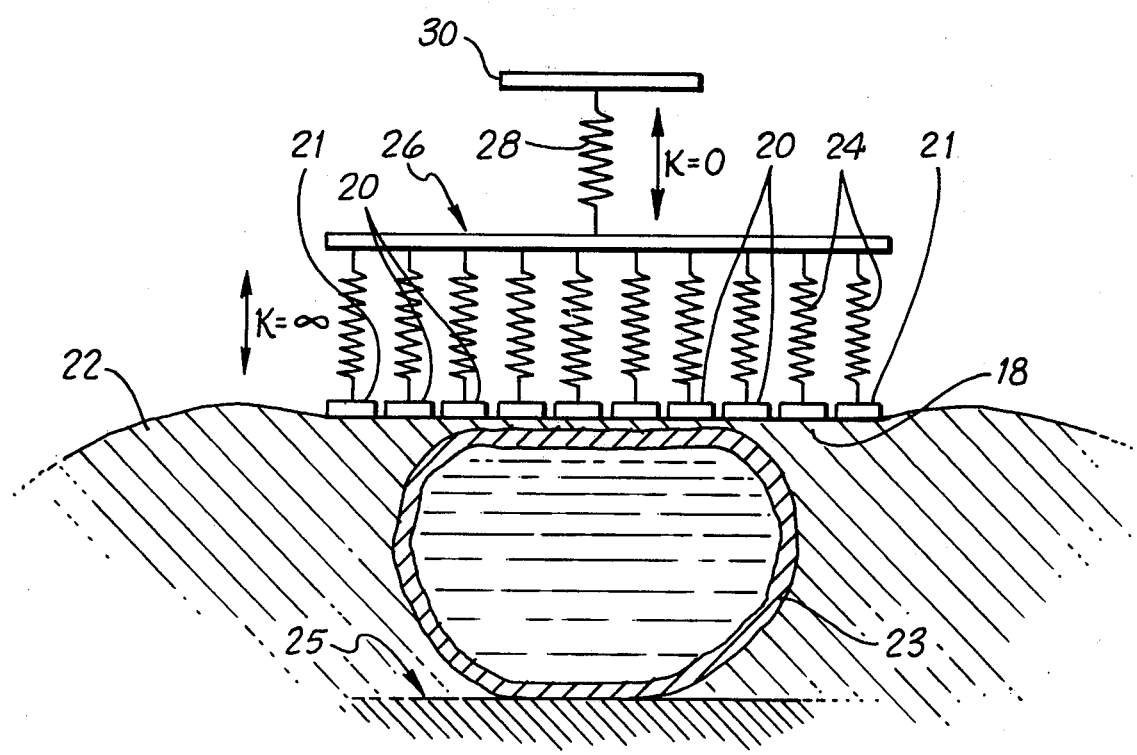
FIG_2

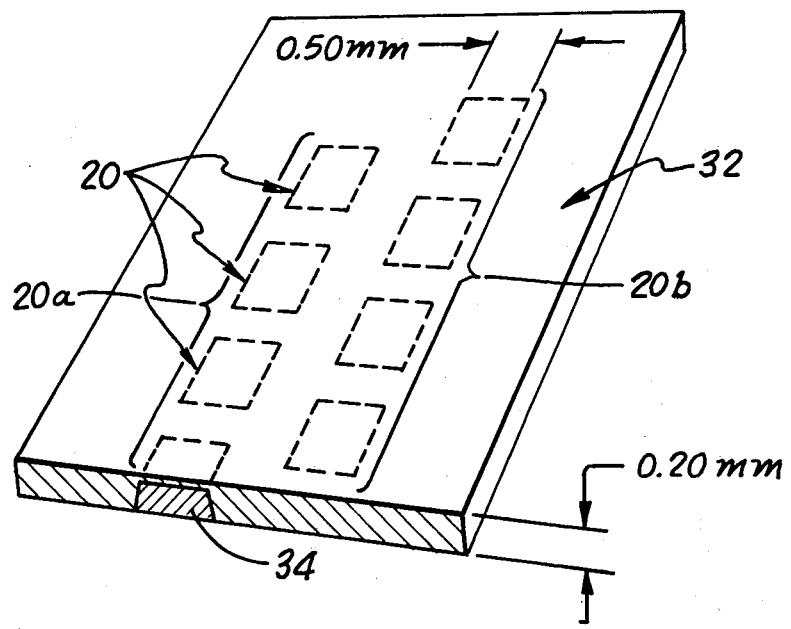
FIG_3
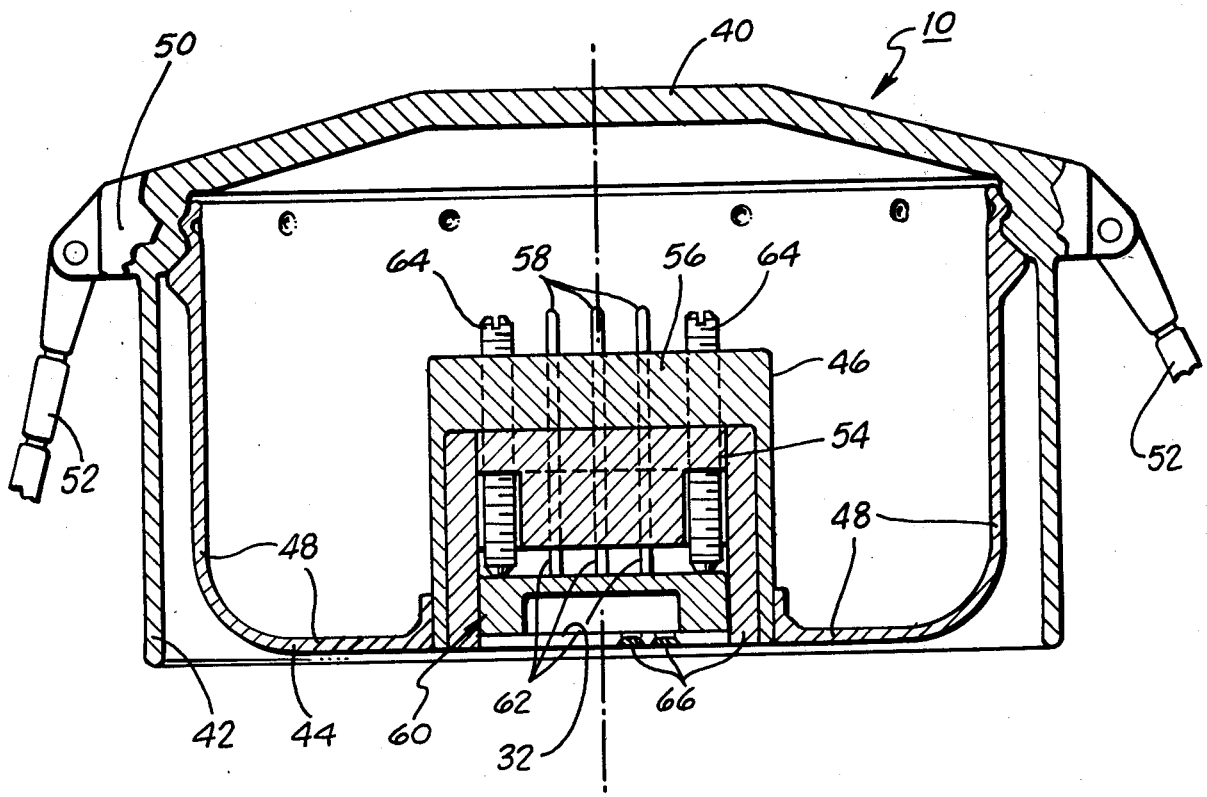
FIG_5

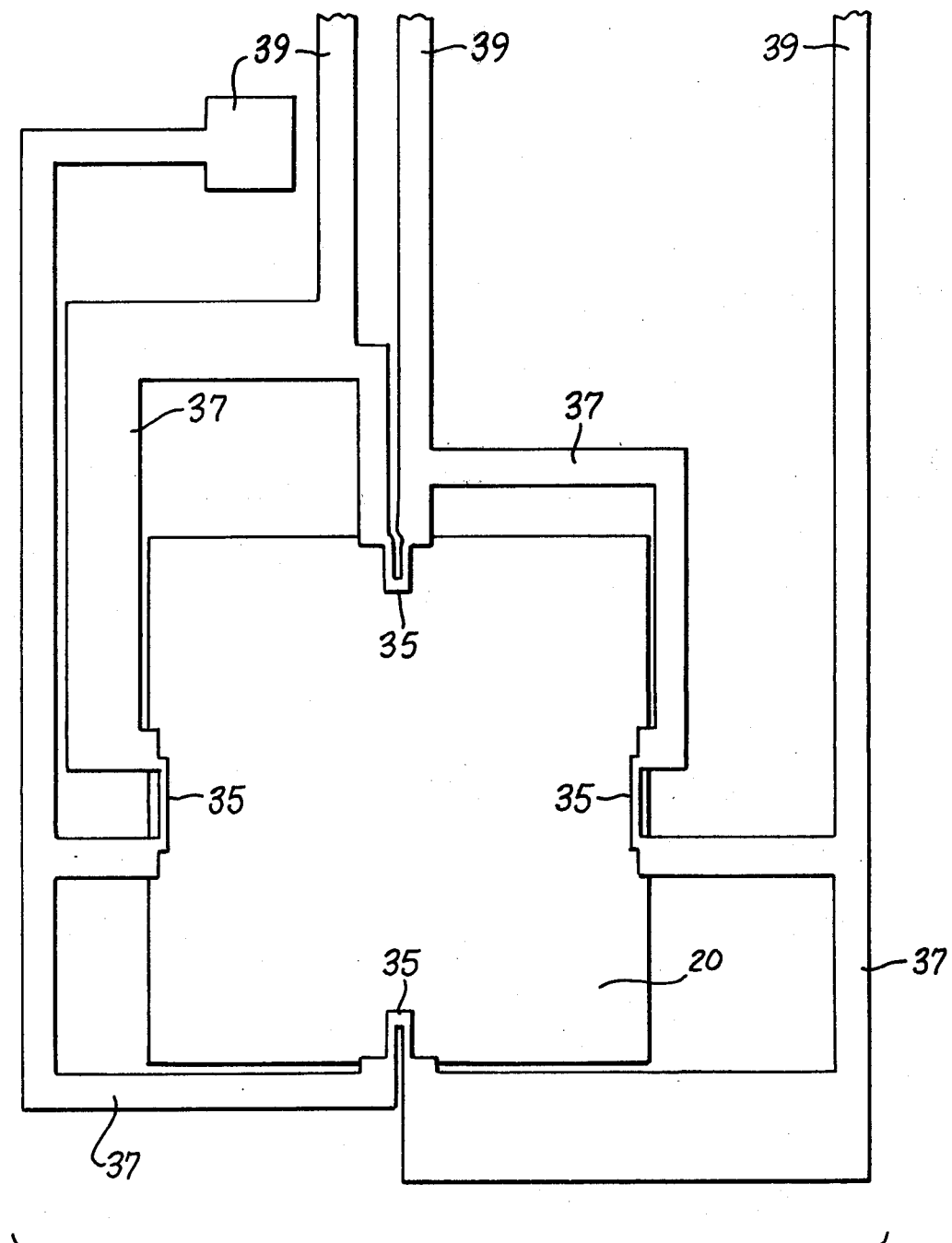

NONINVASIVE BLOOD PRESSURE MONITORING TRANSDUCER

The invention described herein was made in the course of work under a grant or award from the Department of Health, Education, and Welfare.

CROSS REFERENCE TO RELATED APPLICATIONS

This application is a continuation-in-part of Ser. No. 848,754, filed Nov. 4, 1977, and now abandoned.

BACKGROUND OF THE INVENTION

1. Field of Invention

This invention relates to apparatus and method for measuring arterial blood pressure. More particularly, the blood pressure monitor of the present invention allows noninvasive, instantaneous and continuous monitoring of blood pressure and provides for producing a waveform which closely represents the complete blood pressure waveform in a superficial artery.

Continuous, noninvasive blood pressure monitoring and recording are the subject of extensive investigation. Both tonometric and sphygmomanometric techniques are being considered. Where measurements are to be made while the subject is engaged in normal activities and over long periods of time tonometry is the preferred approach, because the pressure transducers used in tonometry can be made small, light and easy to wear, whereas the pressurized cuffs used in sphygmomanometry are relatively uncomfortable and cuff pressure changes required to obtain significant parameters are difficult to produce on a mobile subject. Further, the sphygmomanometer only yields the systolic (highest pressure in the arteries during contraction of the heart muscle) and diastolic (lowest pressure in the arteries during relaxation of the heart muscle) pressures, whereas the entire blood pressure waveform can be reproduced using the tonometric approach.

2. Relation to Prior Art

The invention builds on and represents an improvement on the technique described and claimed in U.S. Pat. No. 3,219,035, issued in the names of Gerald C. Pressman and Peter M. Newgard and assigned to the assignee of the present invention. The invention described in that patent relates to a force-balance technique which provides a noninvasive, precalibrated blood pressure measurement. The force-balance arrangement eliminates variations in blood pressure measurements which are only a result of variations in pressure between the transducer surface and the subject. A somewhat more complex approach to solving the same problem is found in U.S. Pat. Nos. 3,880,145 to Edward F. Blick and 3,123,068 to Robert P. Bigliano. A major difficulty encountered in the application of these devices has been locating an initial position of the measuring transducer element relative to the superficial artery and maintaining its position to obtain the accuracy required.

The invention described and claimed in copending patent application Ser. No. 848,753, filed even date herewith in the name of Peter M. Newgard and assigned to the assignee of the present invention, represents an improvement in the art in that it diminishes the positional accuracy required of the transducer array by at least an order of magnitude. Hence, initial placement of the device is trivial and the transducer design is such that it easily tolerates the nominal variations in position that are encountered during typical long term monitoring applications. Further, the method of selecting the proper waveform from among those produced by the array of individual transducers as set forth in that application is responsible, at least in part, for both diminution of required positional accuracy and tolerance for variations in position due to movements of the subject during monitoring of the pressure.

The present invention constitutes an improvement over both the art and the invention described and claimed in the Newgard application, supra, in that the method and means of selecting the particular pressure sensitive element of the array of transducers which most closely tracks the true blood pressure waveform and gives the most accurate measure of blood pressure are further refined.

SUMMARY OF THE INVENTION

The present invention, a noninvasive arterial blood pressure monitor, incorporates a transducer array for generation of an electrical waveform indicative of blood pressure in the artery and a novel method of determining the waveform from among those generated by individual transducers of the array which most closely matches the actual pressure in the artery. Each individual force sensing element has at least one dimension smaller than the lumen of the underlying artery wherein blood pressure is to be monitored and the individual force sensing element is selected to monitor blood pressure which is within one artery's diameter of the pressure sensing element generating the maximum pulse amplitude and which generates a waveform showing a local minimum of at least one of the diastolic and systolic pressures.

An object of this invention is to provide an externally applied blood pressure measuring transducer which is easy to position for accurate continuous monitoring of arterial blood pressure even on a mobile subject.

Another object of the invention is to provide such a blood pressure measuring transducer wherein an array of individual transducing arterial riders is utilized and a means is provided to select and utilize the arterial rider (pressure sensitive element) which most closely reproduces the actual pressure waveform.

The novel features which are believed to be characteristic of the invention are set forth with particularity in the appended claims. The invention itself, however, both as to its organization and method of operation, together with further objects and advantages thereof, may best be understood by reference to the following description taken in connection with the accompanying drawings, in which:

FIG. 1 shows the external appearance of a blood pressure transducer case, typically positioned over an artery, for providing a continuous external measurement of arterial blood pressure;

FIG. 2 is a schematic diagram illustrating the force balance between artery and the multiple transducer elements (arterial riders), with the artery wall properly depressed to give accurate blood pressure reading;

FIG. 3 is a perspective view of a sectioned transducer chip or substrate showing the array of individual pressure sensitive transducer elements (artierial riders) on the substrate and a preferred arrangement of the individual pressure sensitive elements;

FIG. 4 is a plan view of a portion of the transducer array (silicon chip or substrate) taken directly over one of the individual transducers 20 and showing a transducer bridge and associated circuitry employed in generating and measuring the blood pressure waveform;

FIG. 5 is a central, vertical section taken through the transducer case of FIG. 1 showing the position of the transducer and its supporting components;

Figure 6:
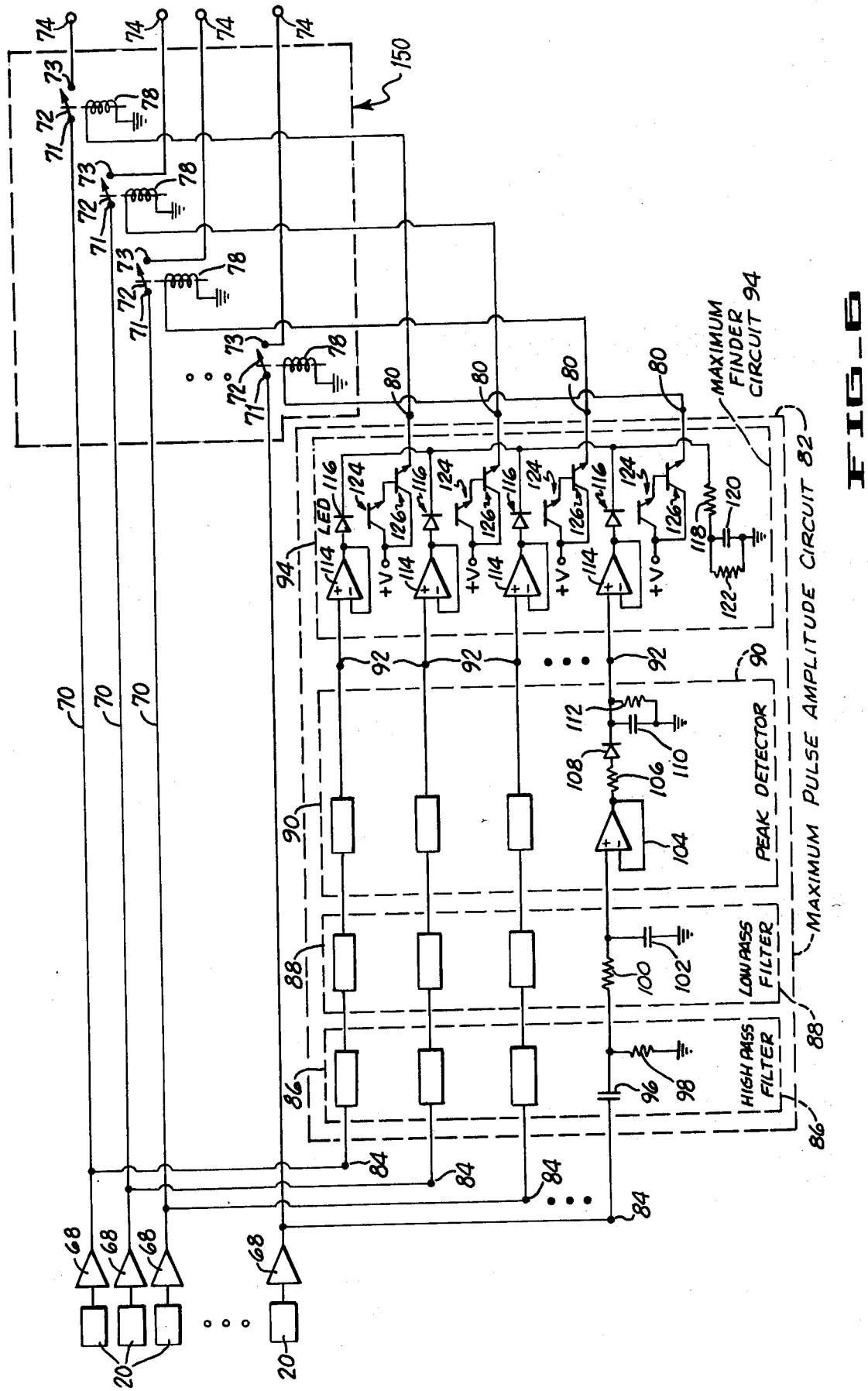
FIG. 6 is a schematic circuit diagram showing circuit elements and their connections which produce a waveform that tracks arterial blood pressure and also selects the pressure sensitive element which produces the waveform with maximum pulse amplitude, along with those pressure sensitive elements immediately surrounding it.
Figure 7:
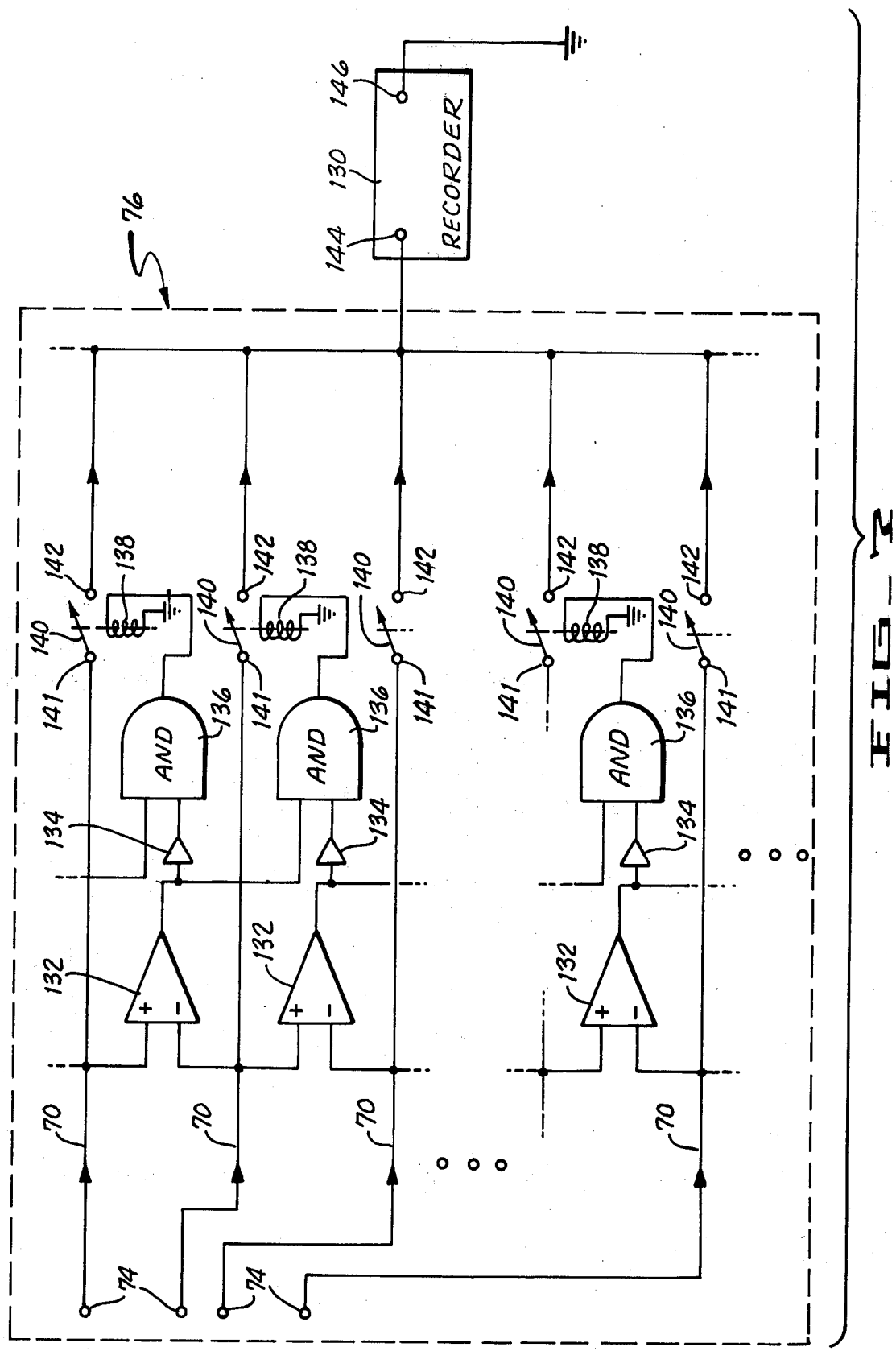
Figure 8:
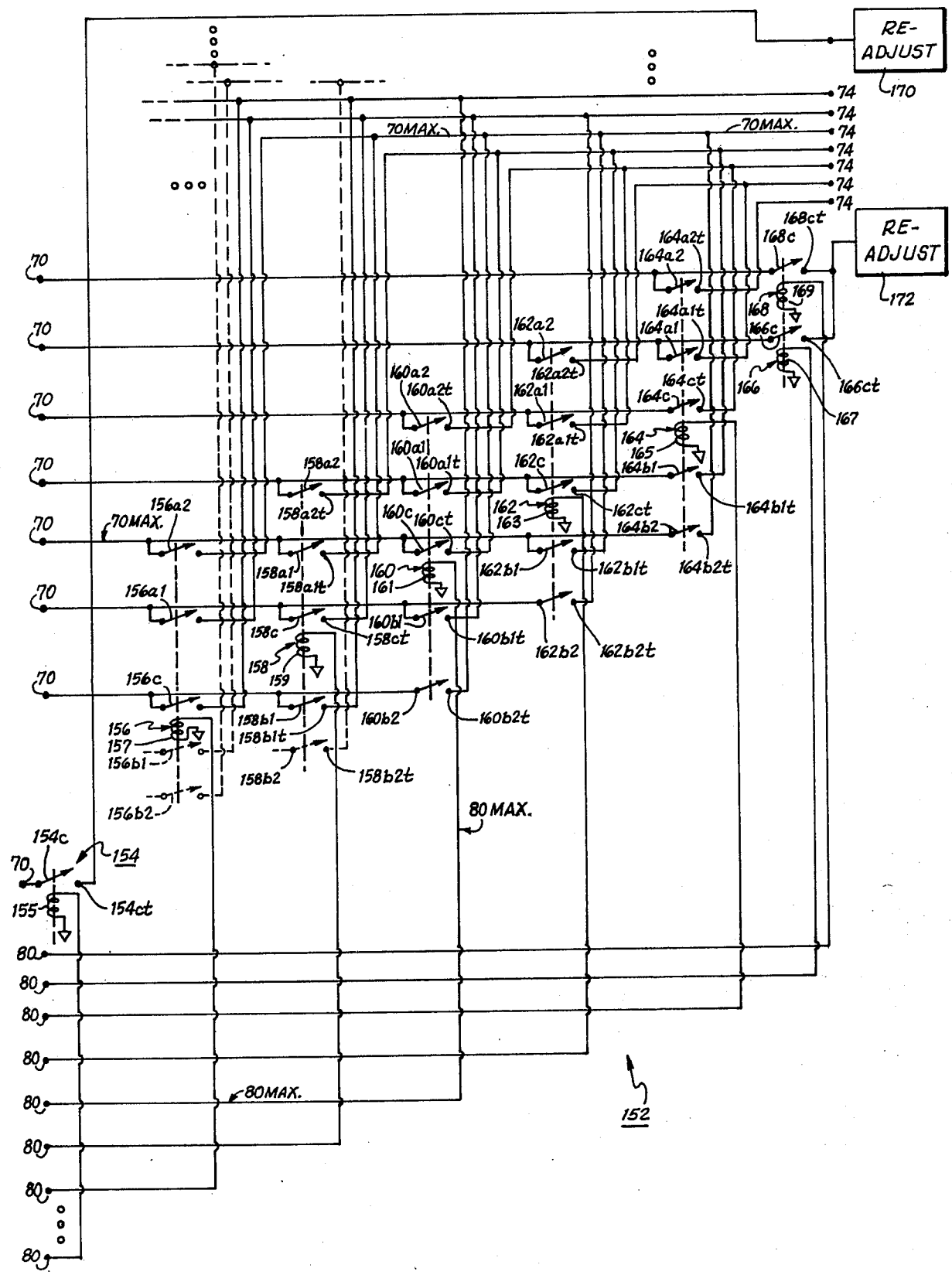

FIG. 7 is a continuation of the schematic diagram of FIG. 6 showing circuit elements which take the output signals from the circuit of FIG. 6, find the waveform which contains a local minimum of diastolic or systolic pressure among those waveforms generated by pressure sensitive elements near the one generating the waveform of maximum amplitude and connect the output of that one pressure sensitive element to a measuring and recording device; and FIG. 8 is a schematic circuit diagram showing a switch matrix which can be substituted for the switches in the diagram of FIG. 6 (the switches 72 enclosed in the broken-line box 150) to ensure that the pressure sensitive elements near the one which generates the waveform of maximum amplitude are connected to the minimum finder circuit of FIG. 7, and hence ensure selection of the pressure sensitive element which generates the waveform most closely representing the complete blood pressure waveform in the underlying artery.

DESCRIPTION OF A PREFERRED EMBODIMENT

A typical application of the transducer array for arterial tonometry is illustrated in FIG. 1 wherein the transducer case 10, which has the appearance of an ordinary wristwatch case, is held in place over the radial artery in a human wrist 12 by an expansion band 14, also similar to that of a wristwatch. Electrical wiring providing connections between the transducer housing 10 and the circuitry (not shown in this figure) for monitoring blood pressure is encompassed in an insulated cord 16 shown emerging from the back of the transducer housing 10. Also enclosed in the cord is a small tube that connects to a source of gas or air (not shown), which source maintains a constant selected pressure in the case 10. The particular location of the transducer case 10 on the body is not critical as long as an artery is covered and contacted with sufficient force to flatten the artery wall without occluding the artery. The artery must be superficial in order to be available for contact, and the transducer must be capable of sensing force applied to the artery. For example, any of the pressure points, such as the temporal or dorsalis pedis artery, may be contacted.

In order better to understand the basic principles of the invention, consider first the diagrammatic mechanical model of FIG. 2, which is representative of factors to be considered in the physical system. The mechanical model will be recognized as that used in the IEEE article by G. L. Pressman and P. M. Newgard entitled "A Transducer for the Continuous External Measurement of Arterial Blood Pressure" (IEEE Trans. Bio-Med. Elec., April 1963, pp. 73–81), adapted to the configuration used in the present invention. For a more complete understanding of the model and its role in the visualization of the elements of the blood pressure measuring system reference should be made to that article, but a brief elementary description is given here.

As shown in the figure, an array 18 of individual pressure sensitive elements or transducers 20, which constitute the arterial riders, is positioned so that one or more of the riders (as shown, four) are entirely over an artery 23. It is emphasized here that the individual riders 20 are small relative to the diameter of the artery 23, thus assuring that at least one of the riders in its entirety is over the artery 23. Findings are that accurate measurement of blood pressure is not only dependent upon so positioning at least one arterial rider but also upon the skin surface 22 and the artery 23 being flattened below the transducers 20. Consequently, the arterial riders 20 and side plates 21 are pressed against the skin surface 22 with sufficient force to cause compression but not occlusion of an underlying artery 23. The use of an array of arterial riders 20, each of which is capable of performing the required measurement, makes positioning of the case 10 trivial.

Pressing the transducers 20 and side plates 21 against the artery 23 with sufficient loading force to flatten the wall, as illustrated, reduces the effect of artery elasticity so that it is not a factor in the measurement and does not appear as a factor in the mechanical model used. In practice, the artery wall 23 responds elastically and acts as if it is resting on a firm base (illustrated by ground symbol 25 under artery 23). Use of the side plates 21 assures that the entire area covered by the transducers 20 will be flattened and, although there is a tangential force from arterial wall tension, it does not affect the vertical force translated and measured by the transducers 20.

As illustrated, the transducer case 10 and mounting strap 14 supply the required compression force and hold the arterial riders 20 and side plates 21 in such a manner that arterial pressure changes are transferred to the arterial riders 20 which overlie the artery 23. Diagrammatically this is illustrated by showing the individual arterial riders 20 and side plates 21 backed by rider spring members 24, a spring backing plate 26 and a backing spring 28 between the backing plate 26 and the mounting strap system 30.

Ideally the coupling (backing spring 28) between the mounting strap system 30 and spring backing plate 26 should be infinitely stiff to restrain the arterial riders 20 and side plates 21 rigidly with respect to the bone structure and, hence, assure that they maintain a fixed position relative to the artery 23. In practice, however, such a system is not practical, and a pneumatic loading system is used which keeps constant the force applied by the mounting strap system 30 to the arterial riders 20 and side plates 21. In the mechanical model the spring constant (k, pressure per unit of deflection) of the backing spring 28 representing such an arrangement is nearly zero. A suitable pneumatic loading system is shown and described in the Pressman-Newgard IEEE article and U.S. Pat. No. 3,219,035, both of which have been previously referenced. The system, therefore, is not described in minute detail in this application.

In order to insure that the arterial riders 20 and side plates 21 flatten the artery and provide a true force measurement (true blood pressure measurement), they must be rigidly mounted. Hence the rider and side plate springs 24 of the model ideally are infinitely rigid (spring constant $k = \infty$). It is found that as long as the system operates in such a manner that it can be simulated by side plate and rider springs 24 having a spring constant on the order of about ten times the value for the artery-skin system, so that the deflection of riders 20 is on the order of 10 microinches, a true blood pressure measurement is obtained.

The actual physical structure of one practical array is shown in a sectioned perspective view in FIG. 3. The array of individual transducers 20 (arterial riders) is formed in a thin (0.20 mm) rectangular (6×8 mm) monocrystalline silicon chip 32 which is made using modern but conventional integrated circuit techniques. Each of the individual transducers or diaphragms 20 in the illustration occupies a square area (0.50 mm square) which is reduced by anisotropic etching to a thickness about 15 microns (1 micron=$1\times10^{-6}$ m). One method which can be used to form such a silicon chip 32 with the thin regions of predetermined thickness in the chip 32 is described in U.S. Pat. No. 3,888,708, issued June 10, 1975 to Kensall D. Wise et al. for "Method for Forming Regions of Predetermined Thickness in Silicon". Contents of this patent are incorporated herein by reference.

The array of transducers 20 in this case is made up of two side by side sets 20a and 20b, each set arranged in a straight line parallel to the other and each individual transducer 20 of one set offset lengthwise (along its straight line), so that the individual transducers of one set (say, 20a) are centered on a line midway in the space between the individual transducers of the other set (20b). The central longitudinal axis of each of the parallel sets 20a and 20b is intended to be positioned essentially perpendicular to the artery 23 where pressure is monitored. In this way the center-to-center spacing of the transducers is less than could be achieved with a single line of transducers. In view of the fact that the individual riders 20 are so small, a number of them will overlie the artery 23 and receive pressure variations due to blood pressure variations in the artery 23. With this arrangement, the transducer case 10 need only be placed generally over the artery to have an arterial rider 20 in optimum position for measurement. In order that the chip 32 present a flat surface to the skin, the depressions formed by etching, that is, the etched area under each individual transducers 20, is filled with a silicone rubber filler 34.

Although the individual transducers 20 may utilize any of the well known stress induced effects, such as piezoelectric, piezoresistive, magnetorestrictive, etc., in the best embodiment of the invention now known, pressure induced stresses (force) on the individual transducers 20 are sensed by piezoresistivity. An understanding of how the piezoresistive effect is utilized may best be had by referring to FIG. 4, which shows a plan view of a part of the silicon substrate or chip 32 that has one of the individual transducers (diaphragms) 20 and the local associated circuitry.

In this embodiment the pressure induced stresses transmitted to the transducer or diaphragm 20 are sensed by a bridge circuit composed of four individual piezoresistors 35 interconnected in conventional bridge circuit form by conductors 37. The output of the bridge circuit appears on the conductors 39, which are taken from the conductors 37 that interconnect the individual resistors 35 of the bridge circuit. The piezoresistive bridge circuit shown is formed on the surface of the silicon substrate 32, which is opposite the surface that contacts the skin of the subject. The resistors 35 and the conductors 37 and 39 of the bridge circuit and its leads are formed by integrated circuit and photolithographic techniques which are now conventional. In the embodiment shown they are formed and interconnected in the manner described in detail in U.S. Pat. No. 3,918,019 and, therefore, the techniques are not described here, particularly since they do not constitute a part of the present invention. The arrangement of resistors 35 and conductors 37 along with the connecting leads 39 thereto is essentially the same for each of the individual transducers 20, and therefore the full circuit pattern on the back of the substrate 32 is not shown here.

The complete silicon substrate 32 with all its interconnected bridge circuits is mounted in what is known in the industry as a conventional dual in line package. The dual in line package is not shown in detail; however, the manner in which the silicon chip 32 and the dual in line package are mounted in the watch-like transducer case 10 is shown in the vertical cross section view of FIG. 5.

The transducer case 10 is generally a cylindrical, hollow container having rigid back and side walls 40 and 42, respectively. The silicon transducer chip 32 is mounted within the face 44 of the case (designated as the front or operative face) in a cylindrical cup-like transducer housing 46. In the practical arrangement shown, the operative face 44 includes a silicon transducer chip 32 along with its included individual transducers are arterial riders 20, the support structure within the transducer housing 46 which surrounds the silicon transducer chip 32 and the portion of the transducer housing support structure on the same face. The pressure sensitive transducers 20 at the operative face 44 of this figure correspond directly to the arterial riders 20 in the mechanical model illustrated in FIG. 2 and the remainder of the operative face 44 which is contained within the housing 46 corresponds to the side plates 21 of FIG. 2.

The transducer housing 46 is fixed to the inside of the transducer case 10 by means of a cup-like silicone rubber bellows 48 which is sealed around the lower outside lip of the cup-shaped transducer housing 46, extends up inside the outer wall of the transducer case 10, and is hermetically sealed to an annular ring 50, which in turn is fixed and sealed to the inside back of the transducer case 10. The flexible silicone rubber bellows 48 being sealed both to the transducer housing 46 and the inside of the transducer case 10 allows air under pressure (air supply to silicone rubber bellows not specifically illustrated) to be introduced into the interior of the case 10 to allow the operative face 44 to be pneumatically loaded, thereby keeping constant the force applied to the arterial riders 20 and side plates 21, thus meeting the criteria established for the model described in connection with the mechanical model of FIG. 2. A mounting strap 52 is affixed to the transducer case 10. The adjusted pneumatic pressure applied inside the silicone rubber bellows 48 supplies the compressional force required to provide the necessary flattening of the artery wall 23.

In order to hold the transducer chip 32 in place and provide for electrical connections to pressure sensitive elements or arterial riders 20, a conventional dual in line package socket 54 is centrally located and fixed to the inside back wall 56 of the cup-shaped aluminum transducer housing 46 with electrical conducting dual in line package socket terminals or pins 58 extending through the back wall 56 of the housing 46 into the pressurized cavity formed by the silicone rubber bellows 48. The dual in line package socket pins 58 are connected by electrical wiring (not shown), which wiring extends from the transducer case 10 through the insulated cord 16 (FIG. 1) to analyzing circuitry (FIG. 6). The transducer chip 32 is fixed to the conventional ceramic dual in line package 60 with its electrical conducting pads making contact with the circuitry of the package 60. Package circuitry is brought out through a series of dual in line package pins 62 that are plugged into the dual in line package socket 54 and thus connected to the dual in line package socket terminal pins 58 and ultimately the analyzing circuitry. The connections in both the ceramic dual in line package 60 and dual in line package socket 54 are conventional, well known in the art and, therefore, not illustrated in detail.

In order to be sure that the face of the silicon transducer chip 32 is properly positioned relative to the rest of the operative face 44, leveling screws 64 (a pair shown, but any required number may be used) are provided and placed so that they extend through the back of the cup-shaped transducer housing 46 and touch the outer edges of the back of the ceramic dual in line package 60. In order to provide a good seal and prevent any electrical leakage of contact between circuits from the transducers 20 to the cup-shaped aluminum transducer housing 46, a silicone filler 66 is provided inside the cup and around the dual in line package socket 54 and package 60.

When the transducer case 10 is held in place on the wrist, generally over the radial artery, as shown in FIG. 1, and the transducer housing 46 is thus supported over the radial artery by the silicone rubber bellows 48, air pressure inside the bellows 48 holds the operative face 44, including the transducer chip 32 and its supporting structure, against the skin surface 22 with sufficient force to achieve the desired degree of flattening of the wall of the artery 23, and individual transducers 20 in the array will each produce an output which is directly responsive to pressure and variations in pressure on the individual transducers. Thus, each of the individual transducers 20 produces an output indicative of the entire pressure waveform exerted thereon.

In accordance with the invention illustrated, described and claimed in the Newgard copending patent application Ser. No. 848,753 supra, the individual transducer or force sensitive element 20 which generates the waveform of maximum amplitude is selected to monitor blood pressure. Using highly refined and sophisticated blood pressure measuring techniques, it has been found that even though the Newgard mode of operation yields good results, the pressure sensitive element 20 which produces the waveform of maximum amplitude is not necessarily the one which is directly over the center of the artery 23 and not necessarily the one which tracks the true arterial pressure with greatest accuracy. Circuitry to carry out the refined selection of the best individual pressure sensitive element 20 to track the blood pressure is illustrated in FIGS. 6 and 7. The portion of the circuit which finds the waveform of maximum amplitude is illustrated in FIG. 6. This part of the circuit is essentially the same as that used in the Newgard copending application Ser. No. 848,753 although, as is described below, it is slightly modified and used in a slightly different way here.

It will, of course, be appreciated that the circuitry shown, while eminently practical, is not to be considered restrictive since the pressure sensitive transducer selection can be carried out in many ways. For example, from a description of the techniques described here, those skilled in the art will be able to program a general purpose computer or to provide a relatively simple, dedicated computer to perform the techniques.

In the circuits of FIGS. 6 and 7 only a few (four) of the individual pressure sensitive transducer elements 20 are shown and, as is conventional, a series of dots is used to indicate that additional elements, along with their circuitry, are used. The number of circuits shown is reduced to simplify the drawings and the explanation. Since the associated circuitry for each of the individual transducer elements 20 is identical, only the circuitry for the first transducer element 20 (bottom in FIG. 6) is shown and described in detail with respect to this figure; the corresponding elements, if shown in other circuits, are given the same reference numerals.

The output of each of the transducer elements 20 is connected directly to an amplifier 68, for the purpose of raising the level of the signal generated to a value more easily handled, and then by a main conductor 70 to one terminal 71 of a normally open switch 72. The opposite terminal 73 of the normally open switch is connected to one of the terminals 74 of a local minimum finder circuit 76 illustrated in FIG. 7. Thus, when any one of the main line switches 72 is closed, the output of the corresponding pressure sensitive element is applied directly to the associated input terminal 74 of the local minimum finder circuit 76 of FIG. 7.

Each of the switches 72 is provided with a closing coil 78 which closes the corresponding switch when energized, and each of the coils 78 is connected between ground potential and a corresponding one of a series of output terminals 80 of a maximum pulse amplitude finder circuit 82, which is illustrated within the confines of the block circumscribed by the broken line so numbered. The input terminals 84 of the maximum pulse amplitude finder circuit 82 are each connected to one of the main line circuit conductors 70 so that the amplified output of each of the individual pressure sensitive transducers 20 is applied to one channel of the maximum pulse amplitude finder circuit 82.

Following the circuit generally from the input terminals 84 through the peak pulse amplitude finder circuit 82, a high pass filter section 86 and then a low pass filter section 88 are first encountered. The output of the low pass filter section 88 is applied directly to a peak detector shown generally in the block 90. The output of the low pass filter 88 is not the pulse amplitude of the output from the pressure sensitive transducer 20 but is proportional to the pulse amplitude. Peak detector 90 receives the pulse output of the low pass filter 88, operates on it, and generates an output which is a direct function of the peak, or maximum value of the applied waveform. Thus, a signal corresponding to the pulse amplitude of the wave generated by each of the pressure sensitive transducers 20 is applied to a corresponding one of the output terminals 92 of the individual peak detector circuits.

The terminals 92 also constitute input terminals for a maximum finder circuit 94, which is the final stage of the maximum pulse amplitude circuit 82. In the copending Newgard application, supra, the function of the maximum finder circuit is to find the one circuit input (at one of the input terminals 92) which has the signal of greatest magnitude and produce a relay enabling (actuating) voltage only at the one specific output terminal 80 in the appropriate circuit. In this manner the particular relay coil 78 is energized to close the switch 72 in the main circuit 70 of the specific pressure sensitive transducer element 20 that is producing the output having the greatest pulse amplitude. Thus, the one pressure sensitive transducer 20 which is producing an output waveform with the maximum pulse amplitude is selected. However, in one embodiment of the present invention the circuit not only selects the one pressure sensitive transducer 20 producing the maximum pulse amplitude waveform but also some transducers 20 which are surrounding it, preferably those within an area which spans substantially the width of the artery 23 being measured.

A better understanding of the circuit operation may be had by considering a functional description assuming that a given one of the individual pressure sensitive transducer elements 20 produces the waveform having the maximum pulse amplitude. Assume, for example, that the waveform of maximum pulse amplitude is generated by the bottom transducer element 20 in the figure. The waveform generated by each of the pressure sensitive transducers 20 is amplified by its associated amplifier 68 and applied to the associated, normally open switch 72 by means of its associated main conductor 70. However, the waveform of maximum pulse amplitude is applied from the bottom pressure sensitive transducer 20 to the bottom one of the switches 72, and the remainder of the switches receive waveforms of lesser pulse amplitude. Further, all of the waveforms generated by the pressure sensitive transducer elements 20 are applied to the associated input terminal 84 of the high pass filter circuit. Again, the lower one of the terminals 84 receives the waveform having the maximum pulse amplitude. The high and low pass filters 86 and 88, respectively, in each of the circuits extract the Fourier components of the applied waveform, which components are near the heart rate frequency. In practice, the high pass filter 86 is not strictly necessary; however, it does remove any high frequency components and reduces circuit noise problems. The filtered waveforms are then applied to the connected peak detector circuit 90, which circuit applies the amplitude of the filtered pulse to the respective output terminals 92. Following the original peak waveform assumption, the lowest output terminal 92 in the figure receives a higher voltage than any of the other output terminals 92.

In the mode of operation for the Newgard invention, the maximum finder circuit 94, which receives the peak detector outputs at the series of terminals 92, is arranged so that only the circuit which receives the maximum amplitude from peak detector 90 generates an output; therefore, under the conditions assumed, the only one of the output terminals 80 of the maximum finder circuit 94 which receives a voltage is the lower one in the figure. As a consequence, none of the switch actuated coils 78 are energized except the lower one in the matrix of coils which is connected to the lower maximum pulse amplitude finder output circuit terminal 80. In contradistinction for the mode of operation of the embodiment of this invention (described here), the circuit elements and biases are chosen so that the individual pressure sensitive transducer elements 20 surrounding the one generating the waveform of maximum pulse amplitude within a span covering the underlying artery 23 produce outputs which energize their associated switch coils 78 and apply a waveform to the associated input terminals 74 of the local minimum finder circuit 76 (FIG. 7).

The circuits utilized and illustrated are conventional and can be found in electronic texts and handbooks. However, for the sake of clarity a circuit suitable for performing each of the functions is illustrated and described.

High pass circuit 86 incorporates a capacitor 96 in a series line followed by a resistor 98 from line to ground. The resistor 98 and capacitor 96 are selected, using well known design principles, so that the corner frequency is approximately 0.1 Hz. The low pass filter 88, as is usual, is designed with a resistor 100 in series on the high side of the line and a capacitor 102 shunted to ground. Again using conventional circuit design techniques, the resistor 100 and capacitor 102 are selected to give a corner frequency between 0.5 and 2.0 Hz.

The output of the filter section is applied to peak detector 90, which incorporates first a conventional isolating voltage follower for accurate voltage amplitude tracking and isolation. Next, a resistor 106 and rectifying diode 108 are connected in series with the voltage follower output to provide a pulsating output voltage that follows the output waveform of the voltage follower 104. This circuit combination is followed by a parallel shunt combination of capacitor 110 and resistor 112 (shunted to ground) which provides a voltage proportional to the peak voltage of the waveform applied to the peak detector 90.

The individual channels of the maximum finder circuit 94 are connected to receive their input from terminals 92 which have the peak voltages applied from peak detector 90. Each of the individual channels in the maximum finder circuit is similar to the circuit of the individual channel in the peak detector 90 and, in fact, forms a peak voltage detector. That is, following any one of the channels from the terminal 92, the circuit incorporates an isolating voltage follower circuit 114 followed by a series diode 116, which in this case is a light emitting diode, a series resistor 118 common to all of the channels, and a shunt capacitor 120 and resistor 122 combination connected to ground. The combination of the shunt resistor 122 and capacitor 120 operates in essentially the same fashion as the corresponding combination (capacitor 110 and resistor 112) in the peak detector circuit, with capacitor 120 being charged to a peak voltage nearly equal to (but not equal to) the greatest voltage applied at the input terminals 92. In this embodiment, the circuit components are so chosen that the light emitting diodes 116 which will conduct over the back bias of the capacitor 120/resistor 122 combination are the ones in the channels which include pressure sensitive elements which are over the artery 23 in question. Still assuming that the lower channel (connecting to the bottom pressure sensitive transducer 20 in the figure) receives the maximum applied voltage, the light emitting diode 116 in the bottommost channel certainly conducts and emits light. A phototransistor 124 is provided adjacent each light emitting diode to receive any light emitted thereby, and each phototransistor has its collector connected to a positive source of voltage (indicated by terminals +V) and its emitter connected to the base of a conventional NPN transistor 126. Note that the collectors of the transistors 126 are also connected to the +V terminal so that they are forward biased, and the emitters of the transistors 126 are connected to the output terminals 80 of the maximum finder circuit 94 and the peak pulse amplitude finder circuit 82. The phototransistors 124 which will be conductive are the ones activated by light from a light emitting diode 116. Under the conditions assumed, the light emitting diode 116 of the bottom channel emits light causing a voltage to be applied to its associated maximum finder circuit terminal 80. In like manner the channel associated with each pressure sensitive transducer 20 which is within the designated span will have a voltage applied at its associated maximum finder circuit terminal 80 and corresponding switches 72 will be closed to apply the outputs generated by the associated pressure sensitive transducers 20 to input terminals 74 of the local minimum finder circuit 76 (FIG. 7).

In order to obtain a better understanding of the invention and of the operation of the local minimum finder circuit 76, make the assumption that all of the input terminals 74 shown receive an input voltage. In fact, only those input teminals in channels with pressure sensitive transducers 20 over the artery 23 being monitored would have an input and the amplitude of each applied waveform would be different. The function of the circuit then is to select from the transducer elements 20 which are close to the one generating the waveform with maximum pulse amplitude that individual transducer 20 corresponding to a minimum of diastolic pressure and apply that waveform to a conventional recorder 130, so that the proper blood pressure waveform with all of its included information may be of record. Note here that the transducer corresponding to a minimum of diastolic pressure is the transducer which measures the blood pressure most accurately. Also, the same one corresponds to a minimum of systolic pressure. Thus, either or both pressures can be used as a selecting parameter, and if a corresponding point in time on all the waveforms generated is used, the proper transducer 20 will still be selected.

Consider first just the circuit elements of the local minimum finder circuit 76 which are between a pair of input terminals 74 (take the upper pair) moving from the input terminals toward the output recorder 130 and consider only the functions performed. Note that corresponding circuit elements between each channel are given the same reference numerals to simplify the description and drawings.

A conventional comparator 132 is connected between adjacent lines to compare the voltage applied to each and generate an output equivalent to a one (1) or a zero (0) in logic terms, depending upon which of its input terminal receives the voltage of greater amplitude. The output of the voltage comparator is applied to a conventional inverter circuit 134, known as a NOT circuit, in its own circuit set and one terminal of a conventional AND gate 136 in the next adjacent circuit set (below). The NOT circuit 134 inverts a received logic one (1) to a zero (0) and vice versa and applies it to a lower terminal of the AND gate 136 of the same set. The upper terminal of each AND gate is connected to the converted output of the comparator circuit from the next adjacent circuit set above. The AND gate 136 produces an output only if both its terminals receive ones (1). The AND gates 136 are each connected to supply a voltage across a switch actuating coil 138. Thus, any AND gate which produces an output closes a switch 140 on its associated terminals 141 and 142 in the main line 70 of the next adjacent channel to complete a circuit from the associated pressure sensitive element 20 to the recorder. Thus, the recorder 130, having its terminals 144 and 146 connected in the main channel circuit 70, records the full waveform generated by the associated pressure sensitive element 20.

Take as a specific example the case where the second channel, or main circuit 70 from the top of the figure is the channel corresponding to the generated input signal (input to terminals 74), which is instantaneously less than both its neighbors (i.e., a local minimum). The comparator circuits 132 between our assumed minimum main line 70 (second from the top) and the channel 70 above produces a logic one (1), since its upper, or + terminal receives a signal greater than its lower (−) terminal. The comparator circuit below the assumed minimum channel 70 produces a zero (0) since its upper terminal receives the lower voltage signal. The output zero (0) of the second comparator circuit is applied both to the upper terminal of the AND gate 136 in the next adjacent circuit set below (not shown) and to the NOT circuit 134 in its immediate circuit set. The NOT circuit 134 inverts (or changes) the received signal to a one (1) which is applied at the lower terminal of the AND gate 136 in the same circuit set.

Since the upper terminal of the AND gate 136 receives a one (1) from both the comparator circuit 132 in the circuit set above and its associated NOT circuit 134, it generates an output which energizes the relay coil 138 to which it is connected. This coil 138 closes switch 140 on its terminal 142 that is connected in the circuit with the one pressure sensitive element 20 having the local minimum (diastolic or systolic pressure) which tracks the blood pressure in the underlying artery most accurately.

No other circuit can be completed because each AND gate 136 receives at least one zero (0) unless a local minimum exists adjacent the circuit set to which it is connected. Regarding this, note that the comparator 132 in the circuit set which sends a local minimum delivers a zero to the AND gate 136 in the next adjacent set below so that it does not produce an output.

An embodiment which is preferred because of its reliability utilizes the same transducer array and much of the same circuitry but differs in two respects:

(1) The components of the maximum finder circuit 94 (FIG. 6) which receive the peak detector outputs at the series of terminals 92 are selected so that only the circuit which receives the peak amplitude from peak detector 90 generates an output. In other words, only one of the output terminals 80 of the maximum pulse amplitude circuit 82 has an output voltage applied from the maximum finder circuit 94, and that one terminal 80 is the one associated with the particular pressure sensitive transducer 20 which generates the waveform of peak amplitude. These are the same conditions that apply with the corresponding circuit in copending Newgard application Ser. No. 848,753.

(2) The switch circuitry enclosed in the broken-line box 150 at the upper righthand side of FIG. 6 is replaced by a switch matrix 152 illustrated in FIG. 8. The function of switch matrix 152 is to make certain not only that the one individual pressure sensitive transducer or arterial rider 20, which generates the waveform of maximum pulse amplitude, is connected to the appropriate input terminal 74 of the local minimum finder circuit 76 (FIG. 7), but also that the elements 20 which surround that one transducer 20, and which elements are within a distance approximately equal to one half the diameter of the underlying artery 23, are also connected to corresponding input terminals 74 of the local minimum finder circuit 76. Thus, the local minimum finder circuit 76 will select (as previously described) the local minimum of diastolic or systolic pressure from among the applied waveforms.

Consider the switch matrix of FIG. 8 and recognize that the input terminals 80 at the lower left of the figure represent output terminals (with like reference numerals) from the maximum pulse amplitude circuit 82 (FIG. 6) and that its output terminals 74 at the upper right side of the figure represent input terminals of the local minimum finder circuit 76 of FIG. 7. The amplified output from the individual arterial riders 20 enter the switch matrix 152 from the left on the lines labeled 70, as in FIG. 6.

Again, the number of individual circuits shown has been reduced for purposes of simplifying the illustration and description. Additional circuits are indicated by the broken-line circuits and the dots between circuits. It is believed that adequate illustration of the point that the individual switches of matrix 152 connect the individual arterial riders 20 which overlie an underlying artery 23 where the pressure is to be monitored requires a larger number of individual circuits in the mmatrix 152 than that required to illustrate operation of the maximum pulse amplitude circuit 82 or the local minimum finder circuit 76. Therefore, more of the individual circuits of the switch matrix 152 are shown than are shown for either the maximum pulse amplitude circuit 82 or the local minimum finder circuit 76, although it is obvious that the actual number of individual circuits must match.

The switch matrix 152, as illustrated, includes a series of individual solenoid operated switches (as illustrated) 154, 156, 158, 160, 162, 164, 166 and 168. Each of these switches have five mechanically ganged contact closing arms. As a matter of convention and uniformity, the center contact arm of each of the switches is designated by the switch number followed by the letter "c", the arms above the center arm are designated by the letter "a" and the ones below by the letter "b", and these letters are followed by the numerals 1 or 2, increasing moving away from the center arm. Thus, the switch 160 (roughly in the center of the matrix 152) has a center contact arm 160c, a contact arm 160a1 for the circuit just above, and a contact 160b1 for the circuit just below. The two outer contact arms of the switch 160 are labeled 160a2 and 160b2 for second circuits above and below, respectively. The kind of switch illustrated is not intended to be limiting, since most any form of switch can be substituted. Certainly, the number of contact arms is not to be considered a limitation, since the number "five" is only illustrative and selected as representative of the number of arterial riders 20 in the array which would overlie the artery 23 where blood pressure is to be monitored.

In order to understand the operation of the usual case, consider a switch matrix where an individual arterial rider 20, somewhere near the center—or at least not too near the edge—of the array of transducers produces the waveform of maximum pulse amplitude. Assume for the illustration that the maximum amplitude waveform appears at the input line labeled "70 Max" of FIG. 8 (fourth line 70 from bottom, not counting the missing circuits represented by the dots in the figure). As described earlier, the maximum pulse amplitude circuit 82 generates a positive voltage at the corresponding output terminal 80 (at line labeled "80 Max", fourth from bottom in the figure). By tracing this circuit it is seen that this voltage is applied across the solenoid 161 (to ground) of the switch 160, which is one of the central switches in the switch matrix 152 as illustrated.

A voltage across the solenoid 161 closes all the switch arms of switch 160 on their associated terminals (given the same numeral as their switch arms with the addition of a "t" for terminals). Thus, the center switch arm 160c closes on its terminal 160ct to connect the maximum amplitude waveform from the circuit 70 Max to the output terminal 74 (trace line 70 Max). The two upper switch arms 160a1 and 160a2 close on their associated terminals 160a1t and 160a2t, respectively, and the two lower switch arms 160b1 and 160b2 close on their associated terminals 160b1t and 160b2t. In this manner, the output waveforms generated by five adjacent arterial riders 20 which overlie the artery 23 in which the blood pressure is being monitored are connected to switch matrix output terminals 74. These terminals 74 are also input terminals of the local minimum finder circuit 76.

As previously described, the local minimum finder circuit 76, using the applied waveforms, finds the individual pressure sensitive element 20 having a local minimum of at least one of the diastolic and systolic pressures and electrically connects that element 20 to the recorder 130 so that the generated waveform is monitored. An inspection of the switch matrix circuit 152 shows that the centrally located switches operate in the same manner to fulfill the objects of the invention. It should be noted, however, that the outer switches 154, 166 and 168, when closed, connect the respective lines 70 to "readjust" signal circuits 170 and 172 rather than to terminals 74 of the minimum finder circuit 76. A readjust signal alerts the operator to the fact that one of the arterial riders 20 which lies on the outer periphery of the array is generating a waveform of maximum pulse amplitude and that the transducer array should be repositioned so that the best possible measurement of pressure is obtained. The readjust alarm devices 170 and 172 may be flashing lights or light emitting diode characters, or any other known type which will indicate a need to reposition the transducer array.

Thus it is seen that the objectives of the present invention have been carried out employing particular embodiments. While these embodiments of the invention have been shown and described, it will, of course, be understood that the invention is not limited thereto since many modifications, both in the circuit arrangement and the instrumentalities employed, may be made. It is contemplated that the appended claims will cover any such modifications as may fall within the true spirit and scope of the invention.

What is claimed is:

1. A system for the continuous external measurement of blood pressure in an underlying artery including at least one array of individual pressure sensitive elements, each of said individual pressure sensitive elements in said array having at least one dimension smaller than the lumen of the underlying artery in which blood pressure is measured and spaced in such a manner that more than one of said individual pressure sensitive elements is over at least a portion of the underlying artery, each of said pressure sensitive elements being capable of producing a continuous waveform having an amplitude which is a function of blood pressure in an underlying artery, and selecting means to select the one pressure sensitive element that has a local minimum of at least one of the diastolic and systolic pressures from the said individual pressure sensitive elements within substantially one artery diameter of the one of said pressure sensitive elements which generates the waveform of maximum pulse amplitude.

2. A system for the continuous external measurement of blood pressure in an underlying artery as defined in claim 1, wherein said selecting means comprises means to select the said one pressure sensitive element that has a local minimum of diastolic pressure.

3. A system for the continuous external measurement of blood pressure in an underlying artery as defined in claim 1, wherein said selecting means comprises means to select the said one pressure sensitive element that has a local minimum of systolic pressure.

4. A system for the continouse external measurement of blood pressure in an underlying artery as defined in claim 1, wherein said selecting means comprises means to select the said one pressure sensitive element that has a local minimum of diastolic and systolic pressure.

5. A system for the continuous external measurement of blood pressure in an underlying artery comprising at least one array of individual pressure sensitive elements, means for selecting the individual pressure sensitive element of said array which generates the waveform of maximum amplitude, and selecting means to select from the said individual pressure sensitive elements within substantially one artery diameter of said individual pressure sensitive element which generates the waveform of maximum pulse amplitude the one pressure sensitive element that generates a signal showing a local minimum of at least one of the diastolic and systolic pressures.

6. A system for the continuous external measurement of blood pressure in an underlying artery as defined in claim 5, wherein said selecting means comprises means to select the said one pressure sensitive element that has a local minimum of diastolic pressure.

7. A system for the continuous external measurement of blood pressure in an underlying artery as defined in claim 5, wherein said selecting means comprises means to select the said one pressure sensitive element that has a local minimum of systolic pressure.

8. A system for the continuous external measurement of blood pressure in an underlying artery as defined in claim 5, wherein said selecting means comprises means to select the said one pressure sensitive element that has a local minimum of diastolic and systolic pressure.

9. A system for the continuous external measurement of blood pressure in an underlying artery including at least one array of individual pressure sensitive elements and selecting means to select from the said individual pressure sensitive elements within substantially one artery diameter of said individual pressure sensitive element which generates the waveform of maximum pulse amplitude the one pressure sensitive element that generates a signal showing a local minimum of at least one of the diastolic and systolic pressures.

* * * * *